United States Patent [19]

Schultze et al.

[11] 3,966,906

[45] June 29, 1976

[54] DISAGGREGATED GAMMA GLOBULIN AND PROCESS FOR PREPARING IT

[75] Inventors: Hermann E. Schultze, Tenerife, Spain; Hans Gerhard Schwick, Marburg an der Lahn, Germany

[73] Assignee: Behringwerke Aktiengesellschaft, Marburg an der Lahn, Germany

[22] Filed: Apr. 8, 1974

[21] Appl. No.: 459,188

Related U.S. Application Data

[63] Continuation-in-part of Ser. No. 115,071, Feb. 12, 1971, abandoned, which is a continuation-in-part of Ser. No. 584,689, Oct. 6, 1966, abandoned, which is a continuation-in-part of Ser. No. 153,214, Nov. 17, 1961, abandoned.

[30] Foreign Application Priority Data

Oct. 11, 1961 Germany .............................. 64342

[52] U.S. Cl. .............................. 424/85; 260/112 R; 260/112 B; 424/87; 424/177

[51] Int. Cl.[2] ..................... A23J 1/06; A61K 37/06; A61K 39/40; A61K 39/42

[58] Field of Search ........................ 424/85, 87, 177; 260/112 R, 112 B

[56] References Cited

UNITED STATES PATENTS 2,065,196 12/1936 Parfentjev ............................ 424/87

OTHER PUBLICATIONS

Williams et al., spec of 623796 filed Oct. 22, 1945 pp. 1–14; paper No. 11, Sept. 23, 1948, 3 pp.

Petermann, J. Phys. Chem., vol. 46, 1942, pp. 183–191.

Petermann, J. Phys. Chem., vol. 45, 1941 pp. 1–8.

Barandun, Vox. Sang. vol. 7, 1962 pp. 157–166, 169.

*Primary Examiner*—Albert T. Meyers
*Assistant Examiner*—A. P. Fagelson
*Attorney, Agent, or Firm*—Curtis, Morris & Safford

[57] ABSTRACT

A disaggregated gamma globulin, suitable for intravenous injection for purposes of therapy and prophylaxis by means of antibodies, prepared by treating a crude gamma globulin fraction of human serum with pepsin, removing lower degradation products by filtration, and then filtering under sterile conditions.

9 Claims, No Drawings

DISAGGREGATED GAMMA GLOBULIN AND PROCESS FOR PREPARING IT

This application is a continuation-in-part of copending application Ser. No. 115,071 filed Feb. 12, 1971, now abandoned, which in turn is a continuation-in-part of application Ser. No. 584,689, filed Oct. 6, 1966, and now abandoned. The latter application in turn is a continuation-in-part of application Ser. No. 153,214, filed Nov. 17, 1961, now abandoned for "Disaggregated Gamma Globulin and Process of Preparing It".

This invention relates to a novel disaggregated human gamma globulin preparation, a method for making it and a process of treatment with said preparation.

It has been known that the gamma globulin fractions of human serum are effective in the prophylaxis and therapy of a great number of infectious diseases owing to their content of antibodies. Though gamma globulin consequently seemed to be ideally suited for use in the prevention and treatment of infectious diseases, results so far obtained have been rather disappointing.

Known antibody-containing gamma globulin preparations from human plasma were suitable for intramuscular administration only, because these preparations, when administered intravenously, frequently caused side effects such as hypotension, nausea, vomiting, pyrexia, rigora, backache and in severe cases even circulatory failures, unconsciousness etc. Simultaneous administration of antihistaminics or of serotonin-antagonists did not mitigate these side-effects.

Intravenous administration of gamma globulin is desirable, however, inasmuch as it makes the antibodies contained in the gamma globulin immediately and fully available for the prevention and treatment of infection diseases and allows a better and more economical use of the gamma globulin. Further, there is no local loss due to proteolysis, the greater efficiency reduces the cost of treatment, and it causes no painful local irritation.

Intramuscular administration on the other hand, is relatively ineffective because the proportion of the amount injected which is actually absorbed by the blood stream is too small and the rate of absorption is too slow. Investigations carried out recently with traceable gamma globulin showed that only about one third of the gamma globulin administered intramuscularly could be detected in the humoral system within the first day. A second third of the quantity was found to enter the blood circulation only with retardation. The remainder could not be detected in the blood circulation and therefore is presumably not available for rapid, specific defense.

A process for preparing a gamma globulin preparation by treating human serum gamma globulin with a small amount of pepsin has been described by Williams et al., Official Gazette 1949, page 871 (626 O.G. 871). This preparation, though it is obtained from a carefully purified starting material (cf. Patent application No. 623,796, filed Oct. 22, 1945, to Williams pages 4 and 5), is suitable for intramuscular injection only (cf. page 872, last line of the publication). It shows a complement-inactivating action high enough to prevent intravenous injection.

The present invention provides a gamma globulin preparation that has none of the disadvantages of prior gamma globulin preparations while retaining the desirable characteristics thereof. We have found that a disaggregated gamma globulin which does not affect the complement system can be prepared by treating a crude gamma globulin fraction of serum obtained by known methods, for example, by precipitation with ammonium sulfate or with an alcohol such as ethyl alcohol, at a pH-value between 3.5 and 5, preferably 3.8 and 4.5, and at a temperature between 25°C and 45°C preferably between 35°C and 45°C, with a quantity of pepsin ranging from about 50,000 to 100,000 preferably 70,000 to 100,000 units, per 100 g of protein to be degraded, while continually controlling the anti-complement activity, for a period ranging from 12 to 48 hours, preferably 20 to 30 hours, until the anti-complement activity has reached a desired low level or even until no anti-complement activity is detectable, removing low molecular weight decomposition products from the disaggregated gamma globulin so obtained, for example by fractional precipitation with neutral salts or organic solvents or by ultrafiltration, filtering under sterile conditions, and lyophilizing if required.

Concerning the admissible limit of complement binding activity of pepsin treated human gamma-globulin the requirements of the Japanese Health Authorities are important. In these Minimum Requirements for Biological Products under paragraph 3.4.6. it is stated:

" 1 ml sample shall be added with 1 ml solution containing 100 units of guinea pig complement, furthermore, 3 ml of an appropriate buffer solution shall be added. When the mixture is tested after being heated for one hour at 30°C, more than 20 units of the complement in the original complement solution must not be inactivated, comparing with the control."

Accordingly it is advisable to lower the complement binding activity in the present process at least below the value of 20 units per milliliter if tested according to the Japanese requirements.

The proteolytic activity of commercial pepsin varies greatly depending on its degree of purity. While any kind of pepsin having a reasonable degree of purity may be used for the degradation of gamma globulin it is important to determine its activity beforehand so as to avoid using too little or too much.

A number of methods are known for the determination of the proteolytic activity of an unknown pepsin to be used in the degradation of gamma globulin. One of these methods is the so-called "Milk Test", which is described in "Biochemische Zeitschrift", 330, 467 et seq. (1958) and which uses the milk-coagulating action of a given pepsin for its determination. This test was applied for the determination of the pepsin used in the present invention, and accordingly the pepsin units mentioned herein are milk tests units (MTU).

Another widely known method is the hemoglobin method described by Northrop in "Crystalline Enzymes", 2nd Edition, New York (1943) pages 303–7. This method uses the degradation of hemoglobin for the determination of pepsin activity. The unit of the activity which is based on this test is commonly referred to as "Anson unit" after the name of the inventor.

Comparative tests made in connection with the present application have shown that different standard pepsins marketed by E. Merck AG., Darmstadt, Germany and standardized to an activity of 1 and 3.5 Anson units per gram exhibited an average activity of 2865 and 10980 MTU per gram, respectively, in the milk test. It results from theses figures that one Anson unit is roughly equivalent to 3000 MTU.

A preferred product of the present invention can be prepared by treating a crude gamma globulin fraction of human serum obtained by known methods, for example, by precipitation with ammonium sulfate, after determination of the anticomplement activity, at a pH-value of 4.0 with 90,000 units of pepsin (MTU) per 100 g of protein to be degraded for 24 hours at 40°C, while continually controlling the anti-complement activity, removing from the disaggregated gamma globulin so obtained, for example by ultracentrifugation, low molecular weight decomposition products, filtering the product under sterile conditions, and lyophilizing it if required. The trademark of this preferred product of the present invention is "Gamma-Venin".

The product of the present invention exhibits the following characteristic properties:

1. It does not affect, or at least does not significantly affect, the complement system of human serum;

2. it contains the whole spectrum of antibodies of the serum of adult humans;

3. it is well tolerated on intravenous administration, as has been proved by a large number of intravenous injections during more than ten year's clinical use;

4. its sedimentation constant S in the ultra-centrifuge predominantly, i.e., for about 80 to 100% of the product, lies in the range of 3.0 to 5.5. Within this range the main product, i.e., about 80 to 88 %, preferably 85 to 88%, has a sedimentation constant between about 5 to 5.3, preferably of 5.3. Since the sedimentation constants used to characterize the product of the present invention form a continuum, i.e., in a graphic reproduction would form a curve, the product (main product as well as the by-components) can be defined by a number of different sedimentation constants and the corresponding percentages. Thus, for example, the main product defined above could as well be defined as that 83% of the product having a sedimentation constant of 5. Besides the main product of the present invention contains negligible amounts of up to about 15 % of by-components which are characterized by lower sedimentation constants, e.g. 12 to 15 % with a sedimentation constant of 3.5, or for example, it may contain 13 % of components with a sedimentation constant of 2. It further may contain very small amounts of by-components with a higher sedimentation constant, for example 4% of compounds with a sedimentation constant of 7–8;

5. it does not inactivate complement factors $C_1'$, $C_2'$, $C_3'$ and $C_4'$;

6. depending on the starting material, it may contain antibodies against the following antigens:

| | |
|---|---|
| diphtheria | streptolysin O |
| tetanus | staphylococci toxin |
| typhus | poliemyelitis type I-III |
| paratyphus | influenza |
| pertussis | parotitis |
| coli | pneumococci |

The good tolerability of the new gamma globulin preparation on intravenous administration results from its tolerability towards the complement system. It is known that gamma globulins of different origin inactivate the complement, especially the complement factor $C'_1$ of human and guinea pig serum. This is true with the main fraction of the known antibody-containing gamma globulin having sedimentation constant S = 7 even if it is prepared under mild conditions, for example, by preparative electrophoresis or by DEAE-cellulose chromatography. To a still higher extent this property is found in those gamma globulin preparations which were heated to 40°–50°C, because heating results in partial aggregation of the gamma globuline particles which in turn is responsible for the occurrence of complement inactivation. Also in the course of the processing of the known gamma globulins, for example, with ethanol, or during storage aggregation products are formed whose sedimentation constants S in the centrifuge are in the range of 8 to 12. The strongest complement inactivation, however, is effected by gamma macro-globulin which belongs to the gamma globulin component system and has a sedimentation constant S of 19 and more.

The complement system is generally considered the source of immune-pathological secondary reactions that follow an antigen-antibody reaction. In these reactions substances leading to anaphylatic reactions are freed enzymatically. Therefore, it is assumed that antibodies that do not affect the complement system also will not cause side reactions. This has in fact been shown with the disaggregated antibody-containing gamma globulin prepared by the process of the present invention.

The difference in the activity of various gamma globulin preparations and the disaggregated gamma globulin of the present invention can be proved by total complement determinations, but it becomes more distinct when comparing individual complement factors, especially the complement factor $C'_1$, determined according to the method described in Klinische Wochenschrift 36, 100 (1958). This method consists in incubating 1 cc. of guinea pig serum (complement) with a determined quantity of gamma globulin, for example 5 mg., at 37° C in a water bath and determining the complement factor activity in samples taken after 1 hour, 3 hours, and 5 hours.

The tolerability of the new gamma globulin preparation is tested in the following manner:

Tolerability

1. Pyrogen test:

The presence of pyrogenic substances is tested i.v. in rabbits with 10 cc of the preparation per kg of body weight.

2. Determination of intravascular blood pressure:

Intravenous injection of 5 cc of the preparation into a rabbit must not alter the blood pressure.

3. Tolerability by animals:

Guinea pigs must tolerate the intravenous injection of 10 cc of the preparation per 400 g of body weight without any serious symptoms. During the following observation period of 7 days no symptoms must be observable.

The new preparation, especially if obtained according to Example 1 ("Gamma-Venin"), is used for the same purposes as the gamma globulin hitherto administered intramuscularly. It is recommended above all for prophylactic purposes and for the mitigation of infectious diseases caused by viruses and bacteria, namely:

| | |
|---|---|
| measles | poliomyclitis |
| hepatitis | viral pneumonia |
| varicelia | viral encephalitis |
| German measles | herpes |
| parotitis | infectious menonucleosis |

-continued

| | |
|---|---|
| suppurating meningitis | herpes zoster, herpes simplex |
| sepsis and osteomyolitis | herpes virus diseases of |
| pneumonia | the eye |

Because of its rapid activity and the fact that it can be administered intravenously in large quantities, the new disaggregated gamma globulin preparation is especially useful in serious cases of sepsis caused by organisms resistant to antibiotics, for example, staphylococci. It may also be used as a substitute for lacking immunizing substances in the case of antibody deficiency syndromes, i.e., A-gamma globulinemia, hypogamma globulinemia, and normo-gamma globulinemia.

Therapeutic or prophylactic administration can be carried out with an injection syringe or by permanent infusion. For the administration of the new preparation, especially if obtained according to Example 1 the normal dosage is about 1 to 3 cubiccentimeters per kilogram of body weight. In special cases the following dosages proved effective:

| Disease | Dosage (cc/kg) | Duration of Protection |
|---|---|---|
| hepatitis (prophylaxis) | 0.02 | 5–9 months |
| measles prophylaxis | 0.2 | 3–10 weeks |
| 4th to 7th day after exposure | 0.2 – 0.4 | |
| later | 0.5 – 1.0 | |
| measles encephalitis | 2 | |
| vaccine reactions | 0.4 – 0.6 | |
| poliomyelitis (prophylaxis) | 0.3 | 1–8 weeks |
| bacterial infections | 0.5 – 2.0, especially 0.6 – 1 (once or repeatedly) | |
| antibody-deficiency diseases (ADS) | 0.5 – 2.0, especially 0.6 – 1 | |

As "bacterial infections", acute septic-toxic general infections (staphylococcal septicemia, colisepsis, soor (trush) septicemia, etc.), acute bacterial organic diseases with predominantly toxic affection of the general condition (pneumonia, mastitis, angine, generalized pyodermia, enterocolitis, peritonitis, Soor (trush) mycosia, burns, etc.), chronic bacterial organic diseases with acute exacerbations and/or toxic affection of the general condition (peribronchitis, pleura-empyema, pulmonary abscess, paranephric abscess etc.) come into consideration. The "antibody-deficiency diseases (ADS)" can be specified as follows: transitory hypogammaglobulinemic ADS (in the case of infants in the first and second trimenon; dose: about 1.0 to 2.0 ml/kg of b.w.); isolated congenital or "acquired" ADS (for permanent treatment, every 3 to 4 weeks a dose of about 0.5 to 1.0 ml/kg of b.w. In the case of acute infections: about 1.0 to 2.0 ml/kg of b.w.); concomitant forms of ADS (for permanent treatment, every 3 to 4 weeks a dose of about 0.5 to 1.0 ml/kg of b.w. In the case of acute infections: about 1.0 to 2.0 ml/kg of b.w.).

The preparation of the present invention in a sterile, pyrogen-free physiologic salt solution, stored at +4°C. to +6°C., is still usable after a 1 year storage.

Using the preferred preparation obtained according to Example 1 (trademark "Gamma-Venin") the further clinical results were obtained:

I. Prophylactic administration 1.2 – 1.5 milliliters of Gamma-Venin per kilogram of body weight were intravenously injected into 40 children incubated with measles, whereupon only 3 of said children fell ill with measles and these only in mitigated form. Instead of showing the clinical picture typical for measles (extended exanthemas, conjuctivitis, bronchitis rhinitis, fever of 39°–40°C. for 5 to 8 days), said children were only attacked by fever of up to 38°C. for 1 to 2 days and weak formation of exanthemas without further complications. Due to the injection of Gamma-Venin, the disease did not break out in the remaining 37 children.

Gamma globulin (Gamma Venin) prophylaxis furthermore lowers the number of transfusion heptitis. Investigations showed that hepatitis was reduced from 10.6 to 4% by adding 10 milliliters of Gamma Venin to the unit before transfusion.

II. Therapeutic use a. Meningitis, sepsis, osteomyelitis, pneumonia

Of 70 children older than 3 months up to 1 year, 40 suffered from suppurating meningitis, 16 from pneumonia with primary abscess formation, and 14 from sepsis or osteomyelitis. In all cases 2 milliliters of Gamma-Venin per kilogram of body weight were intravenously injected and antibiotics were administered. Within every group of the above-mentioned diseases the same antibiotics were administered to each patient.

Suppurating meningitis: Without Gamma Venin fever disappeared after about 5–8 days: with Gamma-Venin already after about 3–4 days.

Sepsis and osteomyelitis: Without Gamma-Venin fever disappeared after 2–3 weeks: with Gamma-Venin already after about 6–8 days. A surgical procedure which otherwise is often necessary could be avoided.

Pneumonia with primary abscess formation: Without Gamma-Venin fever disappeared after about 10 days; with Gamma-Venin already after about 4–5 days. A meteorism occurring in the normal course on the base of a toxic-paralytic ileus, disappeared upon administration of Gamma-Venin. Strongly dyspneic and cyaneic symptoms are likewise reduced or disappear by injection of Gamma-Venin.

b. Viral diseases

Herpes Zoster: Gamma-Venin specifically has an analgesic action. Dose: about 1.0 to 3.0 ml/kg of b.w.

Herpes simplex: Herpes labialis, Gingivostomatitis herpetica, etc.: Gamma-Venin above all prevents the formation of new efflorescences. Dose: about 1.0 ml/kg of b.w. Herpes virus diseases of the eye: (metaherpetic keratitis and iridocyclitis); dose: about 1.0 to 3.0 ml/kg of b.w.

The following examples illustrate the invention but they are not intended to limit it thereto:

EXAMPLE 1

50 liters of human serum were diluted with distilled water to 85 liters, adjusted to 7.0 and mixed with a saturated ammonium sulfate solution until the ammonium sulfate concentration reached 45%.* The precipitated crude gamma globulin fraction was isolated by centrifugation and dissolved in distilled water. The solution was diluted to 70 liters. After determination of the anti-complement activity (cf. table 1), the solution was adjusted to pH 4.0 by means of acetic acid. 90,000 MTU of pepsin per 100 g protein to be degraded were then added and the solution was exposed for 24 hours at 40°C to the proteolytic action of the pepsin. A sample of the reaction mixture was filtered. The filtrate was adjusted to 7.0 and again tested for anti-complement activity. The main quantity of the reaction mixture was then worked up in the same manner as the sample and freed from low molecular weight decomposition products by ultrafiltration. After filtration under sterile conditions, the protein content was adjusted to 5.0 %. The sedimentation constant S of the main component (85 – 88%) of the solution so obtained was 5.3, the sedimentation constant S of the by-component (12 – 15 %) about 3.5. The product obtained according to Example 1 can also be characterized (sedimentation curve) by a main component (about 83 %) with a sedimentation constant S of 5, a by-component (about 13 %) with a sedimentation constant S of 2, and a further by-component (about 4%) with a sedimentation constant of 7 – 8.

*of saturation

The trademark of the product obtained according to Example 1 is "Gamma-Venin".

The yield was 4 liters of a solution of 5% strength of disaggregated gamma globulin, i.e., about 75 % of the gamma globulin contained in the serum, which however no longer affects the complement system. As shown in the following table, the disaggregated gamma globulin does not inactivate the complement system.

Notes to Table 1

The test results indicated in Table 1 show that the tested crude fraction of gamma globulin strongly inactivates the complement. This inactivation of the complement depends on the incubation period. The gamma globulin crude fraction exerts the strongest action on the complements $C'_1$ and $C'_4$. The table further indicates that a disaggregated gamma globulin obtained in accordance with this example no longer has anti-complement activity, and that the test results of the samples taken from the final container correspond to those of the batch.

EXAMPLE 2

50 liters of human serum were diluted with distilled water to 90 l, adjusted to pH 7 and saturated with ammonium sulfate until the ammonium sulfate saturation was 45 %. The precipitate consisting of crude gamma globulin was centrifuged and dissolved in distilled water; the solution was diluted to 65 liters. After determining the complement inactivating activity the solution was adjusted to pH 4.3 by means of hydrochloric acid. 75.000 MTU of pepsin per 100 g substrat were then added and the whole was allowed to stand for 24 hours at 40°C. A sample of the reaction mixture was filtered, the filtrate was adjusted to pH 7.0 and the absence of anti-complement activity was verified. The main body of the reaction mixture was then filtered with charcoal, the filtrate was adjusted to pH 7.0 with sodium hydroxide solution and a saturated ammonium sulfate solution was added until the saturation was 50 %. The protein precipitate was collected and dissolved in distilled water, the solution was filtered germ-free and ultrafiltered. In the purified solution the protein content was adjusted to 5 % by adding glycocoll and sodium chloride. The solution was again filtered under sterile conditions, filled into ampoules and lyophilized. The yield was 4 l of a 5 % solution of disaggregated gamma globulin, i.e. 75 % of the original amount. The product had no effect on the complement system.

The procedure of Example 2 of the application was varied in respect to the following variables:

pH during degradation 3.5 . . . 5.0, amount of Pepsin per 100 g Gammaglobulin (MTU) 50,000 . . . 100,000, degradation time (hours) 12 . . . 48, degradation temperature (°C) 25 . . . 45.

Within this frame tests were carried out wherein the variables were as follows:

| pH | Amount Pepsin | Time hrs. | °C Temp. | Product analyzed as Sample No. |
|---|---|---|---|---|
| test I 5.0 | 50,000 (MTU) | 12 | 25 | E 1 |
| test II 3.5 | 100,000 | 48 | 45 | E 2 |
| test III 4.3 | 75,000 | 24 | 40 | E 3 |

The products were tested for their complement-binding activity by a modification of the method described by A. Nowotny in "Basic Exercises in Immunochemistry", pages 160 – 168, Springer-Verlag, Berlin, Heidelberg, New York (1969).

The test gave the following results:

| | Values found | | | | Average |
|---|---|---|---|---|---|
| E 1 | 14.5 | 30.3 | 53.1 | units | 32.6 ± 15.8 |
| E 2 | 0 | 11.4 | 9.6 | " | 7.0 ± 5.0 |

Table 1

| 1 cc of guinea pig serum | % complement inactivation (37°C) | | | | | | | | | *) | | |
|---|---|---|---|---|---|---|---|---|---|---|---|---|
| | C'1 | | | C'2 | | | C'3 | | | C'4 | | |
| | 1ʰ | 3ʰ | 5ʰ | 1ʰ | 3ʰ | 5ʰ | 1ʰ | 3ʰ | 5ʰ | 1ʰ | 3ʰ | 5ʰ |
| + 0.1 cc = 5 mg of gamma globulin crude fraction | 17 | 65 | 80 | 15 | 30 | 38 | 10 | 25 | 36 | 20 | 37 | 60 |
| + 0.1 cc = 5 mg of disaggregated gamma globulin (sample) | 0 | 0 | 7 | 0 | 0 | 0 | 0 | 0 | 0 | 0 | 3 | 5 |
| + 0.1 cc = 5 mg of disaggregated gamma globulin (batch) | 0 | 0 | 4 | 0 | 0 | 0 | 0 | 0 | 0 | 0 | 0 | 0 |

*) C'1, C'2, C'3 and C'4 are different complement factors of guinea pig serum.
1ʰ, 3ʰ and 5ʰ are reaction periods in hours (ʰ).

-continued

| | Values found | | | | Average |
|---|---|---|---|---|---|
| E 3 | 10.4 | 8.1 | 11.0 | " | 9.8 ± 1.3 |

We claim:

1. The process for preparing a human gamma globulin disaggregated into sub-units by enzymatic action and having no significant effect on the complement system, which process comprises (1) treating a crude antibody-containing gamma globulin fraction of human serum, obtained by precipitating blood serum with ammonium sulfate or alcohol, at a pH between 3.5 and 5 and at a temperature from 25°C. to 45°C. with from 50,000 MTU to 100,000 MTU of pepsin per 100 grams of protein to be degraded, while continually controlling the anticomplement activity, for a period ranging from 12 to 48 hours, until the anti-complement activity, measured by combining a 1 ml sample of the disaggregated gamma globulin with 1 ml of a solution containing 100 units of guinea pig complement in the presence of a buffer solution and heating for 1 hour at 30°C., is such that more than 20 units of the complement in the original complement solution must not be inactivated; (2) removing low molecular weight decomposition products from the disaggregated gamma globulin by filtration; and (3) filtering the disaggregated gamma globulin under sterile conditions.

2. The process of claim 1 wherein the sterile-filtered disaggregated gamma globulin is lyophilized.

3. A process for therapy and prophylaxis utilizing antibodies which comprises intravenously injecting an effective amount of a composition having as its essential active ingredient the disaggregated gamma globulin prepared by the process of claim 1.

4. The process of claim 1 wherein said crude gamma globulin fraction is treated at a pH of 4.0 and a temperature of 40°C. with 90,000 MTU of pepsin per 100 grams of protein to be degraded for 24 hours.

5. The process of claim 4 wherein the sterile-filtered disaggregated gamma globulin is lyophilized.

6. A process for therapy and prophylaxis utilizing antibodies which comprises intravenously injecting an effective amount of a composition having as its essential active ingredient the disaggregated gamma globulin prepared by the process of claim 4.

7. A preparation of human gamma globulin disaggregated into sub-units by enzymatic action and suitable for intravenous injection, prepared by the process of claim 1.

8. The preparation of claim 7 in a sterile, pyrogen-free, physiological salt solution.

9. The preparation of claim 7 in lyophilized form.

* * * * *